(12) United States Patent
Vule et al.

(10) Patent No.: US 11,317,814 B2
(45) Date of Patent: May 3, 2022

(54) SYSTEMS AND METHODS FOR COLLECTING PHYSIOLOGICAL INFORMATION OF A USER

(71) Applicant: BEIJING SHUNYUAN KAIHUA TECHNOLOGY LIMITED, Beijing (CN)

(72) Inventors: Yan Vule, Vancouver (CA); Yoav Aminov, Tel Aviv (IL); Alexander Sromin, Ashdod (IL); Artem Galeev, Vancouver (CA); Elisabeth Dickinson, Vancouver (CA); Ninel Gorev, Ramla (IL)

(73) Assignee: BEIJING SHUNYUAN KAIHUA TECHNOLOGY LIMITED, Beijing (CN)

( * ) Notice: Subject to any disclaimer, the term of this patent is extended or adjusted under 35 U.S.C. 154(b) by 719 days.

(21) Appl. No.: 16/019,284

(22) Filed: Jun. 26, 2018

(65) Prior Publication Data
US 2018/0368701 A1    Dec. 27, 2018

Related U.S. Application Data

(60) Provisional application No. 62/525,795, filed on Jun. 28, 2017, provisional application No. 62/525,483, filed on Jun. 27, 2017.

(51) Int. Cl.
*A61B 5/0205*    (2006.01)
*A61B 5/00*    (2006.01)
(Continued)

(52) U.S. Cl.
CPC .......... *A61B 5/0205* (2013.01); *A61B 5/681* (2013.01); *A61B 5/021* (2013.01); *A61B 5/024* (2013.01);
(Continued)

(58) Field of Classification Search
CPC ......... A61B 5/0205; A61B 5/681; A61B 5/25; A61B 5/021; A61B 5/02405;
(Continued)

(56) References Cited

U.S. PATENT DOCUMENTS

| | | | |
|---|---|---|---|
| 2015/0157220 A1* | 6/2015 | Fish ................... | A61B 5/14552 600/301 |
| 2015/0265214 A1* | 9/2015 | De Kok ................ | A61B 5/681 600/301 |

(Continued)

*Primary Examiner* — Catherine M Voorhees
*Assistant Examiner* — Roland Dinga
(74) *Attorney, Agent, or Firm* — Young Basile Hanlon & MacFarlane, P.C.

(57) ABSTRACT

Described herein are systems and methods for collecting physiological information from a user and determining information including, but not limited to, a user's heart rate, blood pressure, oxygen levels ($SvO_2$), hydration, respiration rate, and heart rate variability. Physiological information is collected from one or more modules, each comprising a sensor array. The sensor array(s) can comprise, among other things, light sources, photo detectors, ECG electrodes/sensors, bio impedance sensors, galvanic skin response sensors, tonometry/contact sensors, accelerometers, pressure sensors, acoustic sensors, and electromagnetic sensors. The information collected from a user can be used to cross-reference a database comprising similar information for a number of subjects as well as verified measurements for each subject including, but not limited to, blood pressure, oxygen levels ($SvO_2$), hydration, respiration rate, and heart rate variability. As such, a user's blood pressure, oxygen levels, hydration, respiration rate, and heart rate variability can be accurately estimated without direct measurement.

14 Claims, 10 Drawing Sheets

(51) Int. Cl.
*A61B 5/1455* (2006.01)
*A61B 5/026* (2006.01)
*A61B 5/0533* (2021.01)
*A61B 5/021* (2006.01)
*A61B 5/024* (2006.01)
*A61B 5/08* (2006.01)
*A61B 5/053* (2021.01)
*A61B 5/25* (2021.01)

(52) U.S. Cl.
CPC ......... *A61B 5/0261* (2013.01); *A61B 5/02405* (2013.01); *A61B 5/053* (2013.01); *A61B 5/0533* (2013.01); *A61B 5/0816* (2013.01); *A61B 5/14551* (2013.01); *A61B 5/25* (2021.01); *A61B 5/4875* (2013.01); *A61B 5/6843* (2013.01); *A61B 2562/0204* (2013.01); *A61B 2562/0219* (2013.01); *A61B 2562/0223* (2013.01); *A61B 2562/0247* (2013.01); *A61B 2562/066* (2013.01)

(58) Field of Classification Search
CPC ..... A61B 5/0261; A61B 5/053; A61B 5/0533; A61B 5/0816; A61B 5/14551; A61B 5/4875; A61B 5/6843; A61B 2562/0204; A61B 2562/0219; A61B 2562/0223; A61B 2562/0247; A61B 2562/066
See application file for complete search history.

(56) References Cited

U.S. PATENT DOCUMENTS

| | | | |
|---|---|---|---|
| 2015/0265217 A1* | 9/2015 | Penders | A61B 5/7221 600/301 |
| 2015/0335283 A1* | 11/2015 | Fish | A61B 5/02444 600/324 |
| 2015/0335284 A1* | 11/2015 | Nuovo | A61B 5/7264 600/301 |
| 2017/0164850 A1* | 6/2017 | Murphy | A61B 5/0245 |
| 2017/0209053 A1* | 7/2017 | Pantelopoulos | A61B 5/02125 |
| 2018/0085058 A1* | 3/2018 | Chakravarthi | A61B 5/150022 |

* cited by examiner

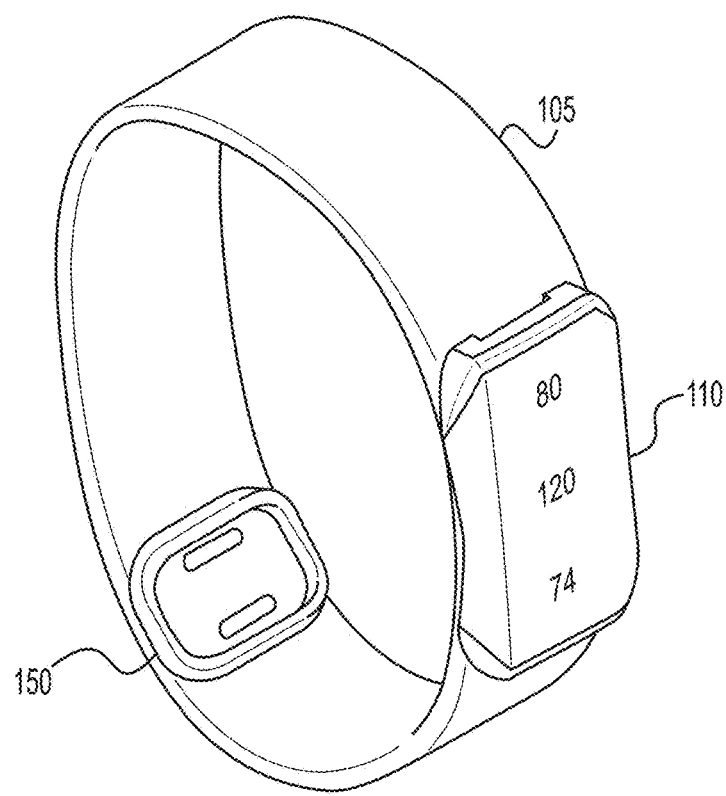
FIG. 5A
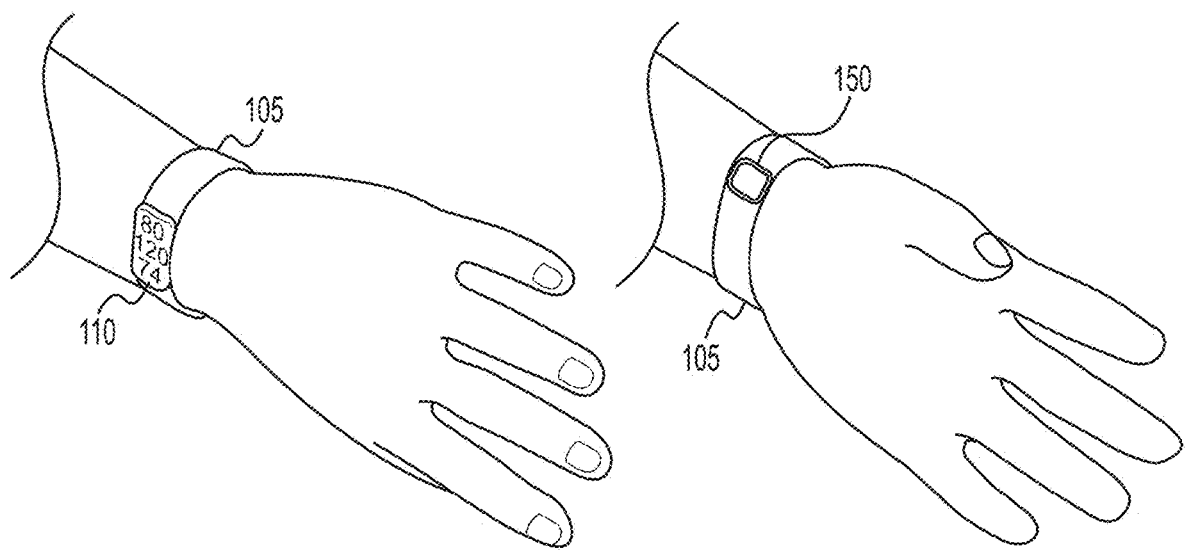
FIG. 5B  FIG. 5C

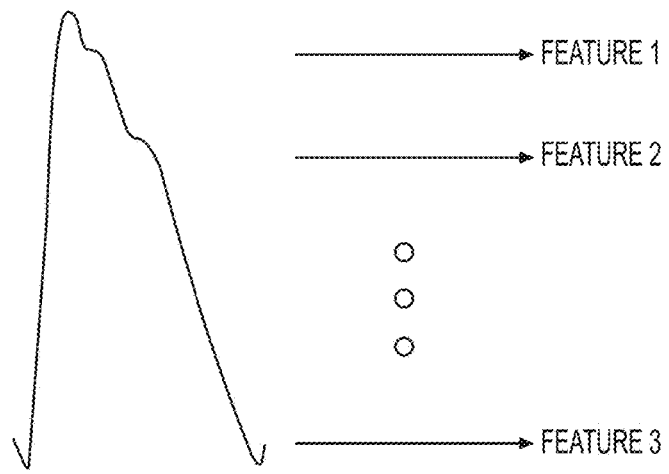
FIG. 6A
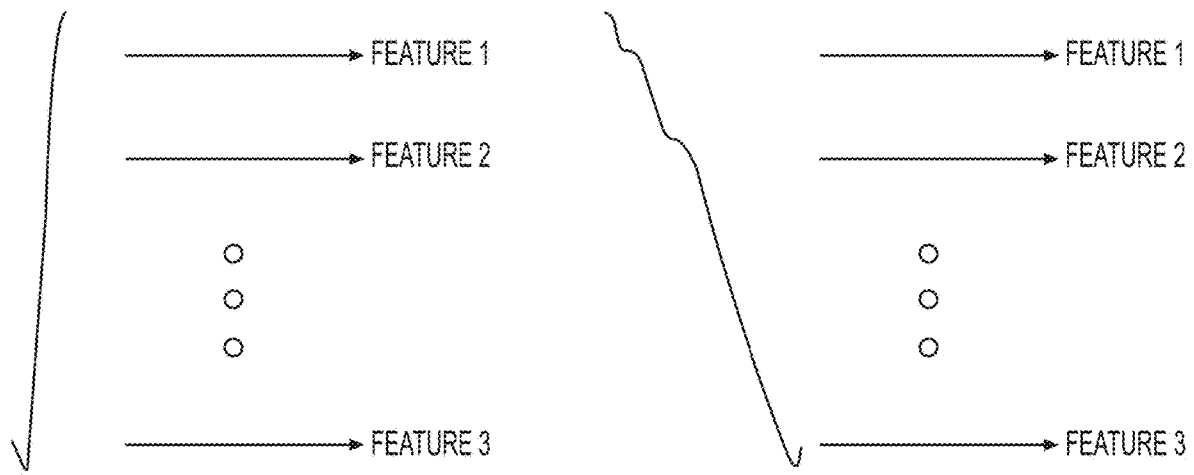
FIG. 6B  FIG. 6C

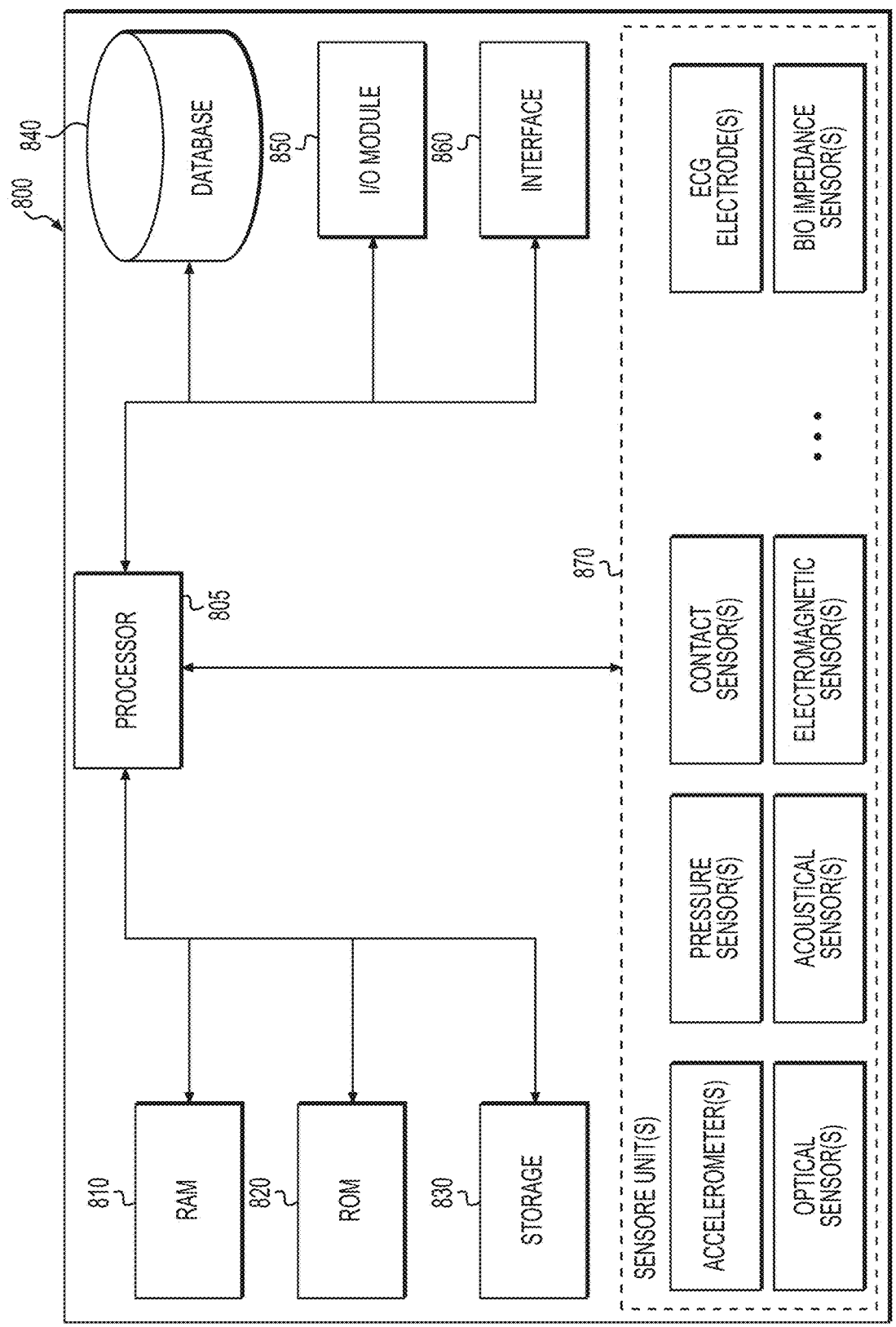

SYSTEMS AND METHODS FOR COLLECTING PHYSIOLOGICAL INFORMATION OF A USER

This non-provisional application claims the benefit of priority to U.S. Provisional Patent Application No. 62/525,483, filed Jun. 27, 2018, and U.S. Provisional Patent Application No. 62/525,795, filed Jun. 28, 2017, both of which are expressly incorporated herein by reference.

FIELD OF THE DISCLOSURE

The embodiments relate generally to systems and methods for detecting physiological information from a user through a number of sensors, analyzing and/or measuring the detected information, and interpreting the information. In one embodiment, the devices described herein include a watch, strap, or band that comprises a number of sensors, including but not limited to one or more of a PPG sensor, an ECG sensor, a pressure sensor, an acoustic sensor, and/or other suitable physiological sensors. The devices can include a pair of modules: an upper module that can be positioned on the top or outside of the wrist; and a lower module that can be positioned on the underside or inside of the wrist.

BACKGROUND

Many portable devices have been developed in which optical sensors are used to detect variation in blood flow through arteries or blood volume in subcutaneous tissue. Applications include the monitoring of heart rate, glucose level, apnea, respiratory stress, and other physiological conditions. The optical sensors often comprise one or more light sources that illuminate a targeted portion of the human body and one or more associated optical detectors that receive a portion of the optical energy emitted by the light sources.

There are two basic types of such arrangements. In transmissive sensor arrangements, a relatively thin portion of the body such as the tip of the finger or the earlobe is positioned between a light source and a photo detector. Light that passes through the body tissue impinges on the photo detector resulting in an electrical signal that is synchronized to each heartbeat. In reflective sensor arrangements, a sensor that includes one or more light sources located in spaced apart juxtaposition with a photo detector is positioned against a targeted area of the body. Optical energy emitted by the light sources passes through the skin of the targeted tissue region, is scattered, partially absorbed, and is reflected by blood flowing through arteries and other vascular structure. The reflected optical energy is in effect modulated in accordance with blood flow in the targeted area and detected by the photo detector. The detected reflection can then be used to produce a signal pulse that is indicative of a physiological parameter such as a heartbeat. In both transmissive and reflective arrangements, the signal produced by the photo detectors is processed to display or otherwise provide a real-time indication of the monitored physiological parameter.

One area of growing interest in the use of physiological monitors is with respect to personal wellness and/or physical exercise for purposes of fitness training, weight loss, or monitoring general health. Technological advances relating to optical sensors, signal processing, and display devices have made it possible to realize small, light-weight physiological monitors that can be embodied as devices that may be worn by a user. Such wearable devices may include, for example, wrist watches, bracelets, and arm bands.

Providing physiological monitors for wellness and physical exercise applications is subject to numerous design and manufacturing considerations. For example, the electronic circuitry for processing the signal produced by the photo detector and displaying an indication of the monitored parameter must operate at a low power level to provide adequate battery life while simultaneously providing sufficient accuracy. Constraints relating to the physical design of such monitors are not limited to the challenges of packaging the electronics and display units in an arrangement that can be worn by a user. Special considerations and constraints are present with respect to incorporation of the optical sensor, including but not limited to variations in physiological features across a large number of users. Moreover, sensor designs that can accurately interpret or predict not just heart rate but other physiological parameters such as calorie expenditure, body movement, heart rate variability, respiration rate, blood pressure, and oxygen level have not been developed.

Therefore, a need exists for improved devices and techniques for incorporating various sensor arrangements in physiological monitoring devices. Moreover, improved device and techniques are needed to ensure the accuracy, reliability, and durability of such devices.

SUMMARY OF THE DISCLOSURE

In accordance with certain embodiments of the present disclosure, sensor arrangements suited for use in physiological monitoring devices that are used for physical training, exercise, and/or general health and wellness monitoring are disclosed. In some embodiments, the monitoring devices may be a wrist watch, bracelet, or arm band comprising one or more sensor arrangements. Each sensor arrangement may comprise one or more sensors, including but not limited to light sources, photo detectors, ECG electrodes/sensors, bio impedance sensors, galvanic skin response sensors, tonometry/contact sensors, accelerometers, pressure sensors, acoustic sensors, and electromagnetic sensors. In such embodiments, the light sources may comprise two or more spaced apart light emitting diodes (LEDs). Each photo detector may be, for example, a photodiode. In some embodiments, each photodiode may be positioned near a corresponding LED or between a corresponding pair of LEDs.

In some embodiments, one or more of the sensor components can be mounted in a transparent lens that may be installed in a portion of a monitoring device configured for placement in contact with a user's skin. Other sensor components may be in direct contact with the user's skin.

In another aspect, the embodiments described here can comprise at least two modules, each comprising one or more sensor components. For example, a device can contain both an upper and lower module. The two modules can be configured such that they are in contact with opposing sides of a user's wrist or other body part when worn by the user. The modules may share common sensor components with respect to one another, or may contain one or more sensor components not found in the other module. In further embodiments, the modules may be in communication with one another. As a result, sensor components from one module can be used to detect reflective light originating from the same module or transmissive light transmitted by the other module.

Additional objects and advantages of the present disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are illustrative and explanatory only and are not restrictive of the claims.

The accompanying drawings, which are incorporated in and constitute a part of this specification, illustrate several embodiments and together with the description, serve to explain the principles of the disclosure.

BRIEF DESCRIPTION OF THE DRAWINGS

FIGS. 5A-5C depict some aspects of an illustrative embodiment of an apparatus as described herein.

FIG. 6A-6C depict some aspects of an illustrative embodiment of an apparatus as described herein.

FIG. 8 depicts an illustrative embodiment of a computing system as described herein.

DESCRIPTION OF THE EMBODIMENTS

Figure 1:
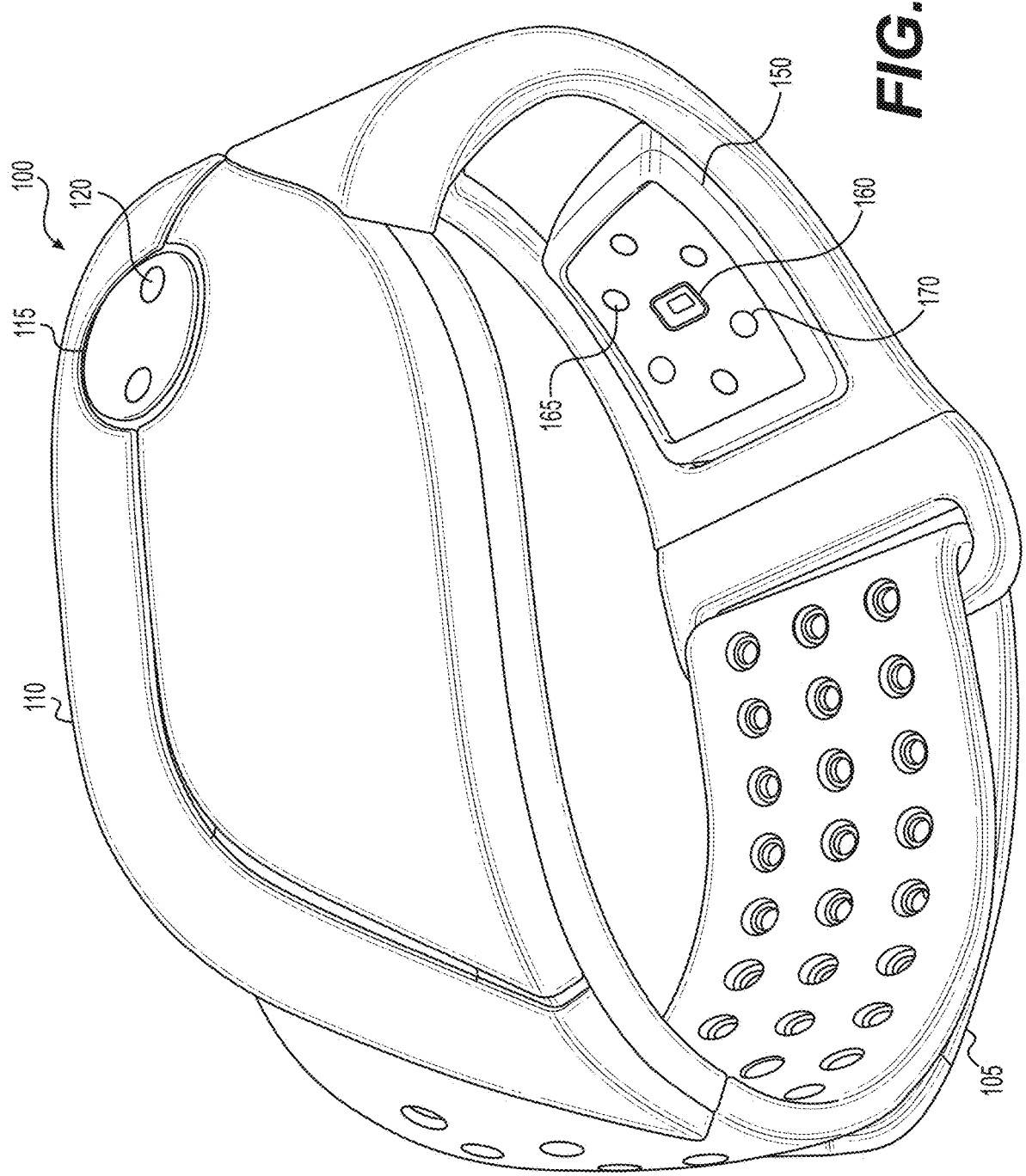
FIG. 1 depicts some aspects of an illustrative embodiment of an apparatus as described herein.

Disclosed herein are embodiments of an apparatus for sensing, measuring, analyzing, and displaying physiological information. In one aspect, the apparatus may be a wearable device comprising an upper module and a lower module. The wearable device may be worn on a user's body such that one or more sensors of the upper and lower modules contact a targeted area of tissue. In one embodiment, the wearable device is a watch, band, or strap that can be worn on the wrist of a user such that the upper and lower modules are each in contact with a side of the wrist. For example, one or more sensors of the upper module may be in contact with or adjacent to the outer portion of the user's wrist and one or more sensors of the lower module may be in contact or adjacent to the inner portion of the user's wrist.

Each of the upper and lower modules may comprise one or more sensors, including but not limited to optical/PPG sensors, ECG sensors/electrodes, bio impedance sensors, galvanic skin response sensors, tonometry/contact sensors, accelerometers, pressure sensors, acoustic sensors, and electromagnetic sensors. In one embodiment, one or more optical/PPG sensors may comprise one or more light sources for emitting light proximate a targeted area of tissue and one or more optical detectors for detecting either reflected light (where an optical detector is located on the same side of the targeted area as the light source(s), i.e., within the same module) or transmitted light (where an optical detector is located opposite the light source(s), i.e., within an opposing module).

In a further aspect, the strap or band of the wearable device may be configured so at to facilitate proper placement of one or more sensors of the upper and/or lower modules while still affording the user a degree of comfort in wearing the device. In one embodiment, rather than a strap that lies in a plane perpendicular to the longitudinal axis of the user's wrist or arm (as is the case with traditional wrist watches and fitness bands), the band may be configured to traverse the user's wrist or arm at an angle that brings one or more components of the upper or lower modules into contact with a specific targeted area of the user while allowing another portion of the band to rest at a positon on the user's wrist or arm that the user finds comfortable.

In another aspect, the precise location of the upper and/or lower modules can be customized such that one or more sensors of either module can be placed in an ideal location of a user, despite the physiological differences between body types from user to user.

The aforementioned features result in more comfortable wearable device while also increasing reliability and accuracy of the device sensing, measuring, analyzing, and displaying of physiological information.

In one embodiment, the physiological information sensed, measured, analyzed, or displayed can include but is not limited to heart rate information, ECG waveforms, calorie expenditure, step count, speed, blood pressure, oxygen levels, pulse signal features, and respiration rate. In other embodiments, the physiological information may be blood pressure information. In further embodiments, the physiological information may be any information associated with a physiological parameter derived from information received by one or more sensors of the wearable device. Regardless, the physiological information may be used in the context of, for example, health and wellness monitoring, athletic training, physical rehabilitation, and patient monitoring. Of course, these examples are only illustrative of the possibilities and the device described herein may be used in any suitable context.

While the systems and devices described herein may be depicted as wrist worn devices, one skilled in the art will appreciate that the systems and methods described below can be implemented in other contexts, including the sensing, measuring, analyzing, and display of physiological data gathered from a device worn at any suitable portion of a user's body, including but not limited to, other portions of the arm, other extremities, the head, and/or the chest.

Reference will now be made in detail to certain illustrative embodiments, examples of which are illustrated in the accompanying drawings. Wherever possible, the same reference numbers will be used throughout the drawings to refer to the same or like items.

FIG. 1 depicts an illustrative embodiment of an apparatus 100. In one aspect, apparatus 100 may be a physiological monitor worn by a user to sense, collect, monitor, analyze, and/or display information pertaining to one or more physiological parameters. In the depicted embodiment, apparatus 100 may comprise a band, strap, or wrist watch. In further embodiments, apparatus 100 may be any wearable monitor device configured for positioning at a user's wrist, arm, another extremity of the user, or some other area of the user's body.

In another aspect, apparatus 100 may comprise an upper module 110 and a lower module 150, each comprising one or more components and/or sensors for detecting, collecting, processing, and displaying one or more physiological parameters of a user and/or other information that may or may not be related to health, wellness, exercise, or physical training sessions.

In addition to upper module 110 and lower module 150, apparatus 100 may comprise a strap or band 105 extending from opposite edges of each module for securing apparatus 100 to the user. In one embodiment, band(s) 105 may comprise an elastomeric material. In alternative embodiments, band(s) 105 may comprise some other suitable material, including but not limited to, a fabric or metal material.

Upper module 110 or lower module 150 may also comprise a display unit 112 for communicating information to the user. Display unit 112 may be an LED indicator comprising a plurality of LEDs, each a different color. The LED indicator can be configured to illuminate in different colors depending on the information being conveyed. For example, where apparatus 100 is configured to monitor the user's heart rate, display unit 112 may illuminate light of a first color when the user's heart rate is in a first numerical range, illuminate light of a second color when the user's heart rate is in a second numerical range, and illuminate light of a third color when the user's heart rate is in a third numerical range. In this manner, a user may be able to detect his or her approximate heart rate at a glance, even when numerical heart rate information is not displayed at display unit 112, and/or the user only sees apparatus 100 through his or her peripheral vision.

In addition, or alternatively, display unit 112 may comprise a display screen for displaying images or characters to the user. Display unit 112 may further comprise one or more hard or soft buttons or switches configured to accept input by the user.

Apparatus 100 may further comprise one or more communication modules. In some examples, each of upper module 110 and lower module 150 comprise a communication module such that information received at either module can be shared with the other module. One or more communication modules can also be configured to communicate with other devices such as the user's cell phone, tablet, or computer. Communications between the upper and lower modules can be transmitted from one module to the other wirelessly (e.g., via Bluetooth, RF signal, WiFi, etc.) or through one or more electrical connections embedded in band 105. In a further embodiment, any analog information collected or analyzed by either module can be translated to digital information for reducing the size of information transfers between modules. Similarly, communications between either module and another user device can be transmitted wirelessly or through a wired connection, and translated from analog to digital information to reduce the size of data transmissions.

As shown in FIG. 1, lower module 150 can comprise an array of sensors 155 including but not limited to one or more optical detectors 160, one or more light sources 165, and one or more contact pressure/tonometry sensors 170. These sensors are only illustrative of the possibilities, however, and lower module may comprise additional or alternative sensors such as one or more acoustic sensors, electromagnetic sensors, ECG electrodes, bio impedance sensors, galvanic skin response sensors, and/or accelerometers. Though not depicted in the view shown in FIG. 1, upper module 110 may also comprise one or more such sensors and components on its inside surface, i.e. the surface in contact with the user's tissue or targeted area.

In some embodiments, the location of sensor array 155 or the location of one or more sensor components of sensor array 155 with respect to the user's tissue may be customized to account for differences in body type across a group of users. For example, band 105 may comprise an aperture or channel 175 within which lower module 150 is movably retained. In one embodiment, lower module 150 and channel 175 can be configured to allow lower module 150 to slide along the length of channel 175 using, for example, a ridge and groove interface between the two components. In this manner, and as described in more detail below, where the user desires to place one more components of sensor array 155 at a particular location on his or her wrist, lower module 150 can be slid into the desired location along band 105. Though not depicted in FIG. 1, band 105 and upper module 110 can be similarly configured to allow for flexible or customized placement of one or more sensor components of upper module 110 with respect to the user's wrist or targeted tissue area.

In addition to the sensors and components proximate or in contact with the user's tissue, upper module 110 and/or lower module 150 may comprise additional sensors or components on their respective outer surfaces, i.e. the surfaces facing outward or away from the user's tissue. In the embodiment depicted in FIG. 1, upper module 110 comprises one such outward facing sensor array 115. In one embodiment, sensor array 115 may comprise one or more ECG electrodes 120. Similar to the sensor arrays of the upper and lower modules proximate or in contact with the user's tissue, outward facing sensor array 115 may further comprise one or more contact pressure/tonometry sensors, photo detectors, light sources, acoustic sensors, electromagnetic sensors, bio impedance sensors, galvanic skin response sensors, and/or accelerometers.

The outward facing sensors of sensor array 115 can be configured for activation when touched by the user (with his or her other hand) and used to collect additional information. For example, where lower module 150 comprises one or more optical detectors 160 and light sources 165 for collecting PPG and heart rate information of the user, outward facing sensor array 115 of upper module 110 may comprise ECG electrodes 120 that can be activated when the user places a fingertip in contact with the electrodes. While the optical detectors 160 and light sources 165 of lower module 150 can be used to continuously monitor blood flow of the user, outward facing sensor array 115 of upper module 110 can be used periodically or intermittently to collect potentially more accurate blood flow information which can be used to supplement or calibrate the measurements collected and analyzed by inward facing sensor array 155 of lower module 150.

In addition to the sensor components described above with respect to each module, each module may further comprise other components for receiving, storing, analyzing, and/or transmitting physiological information. Some of those components are described below with respect to FIG. 8.

Figure 2:
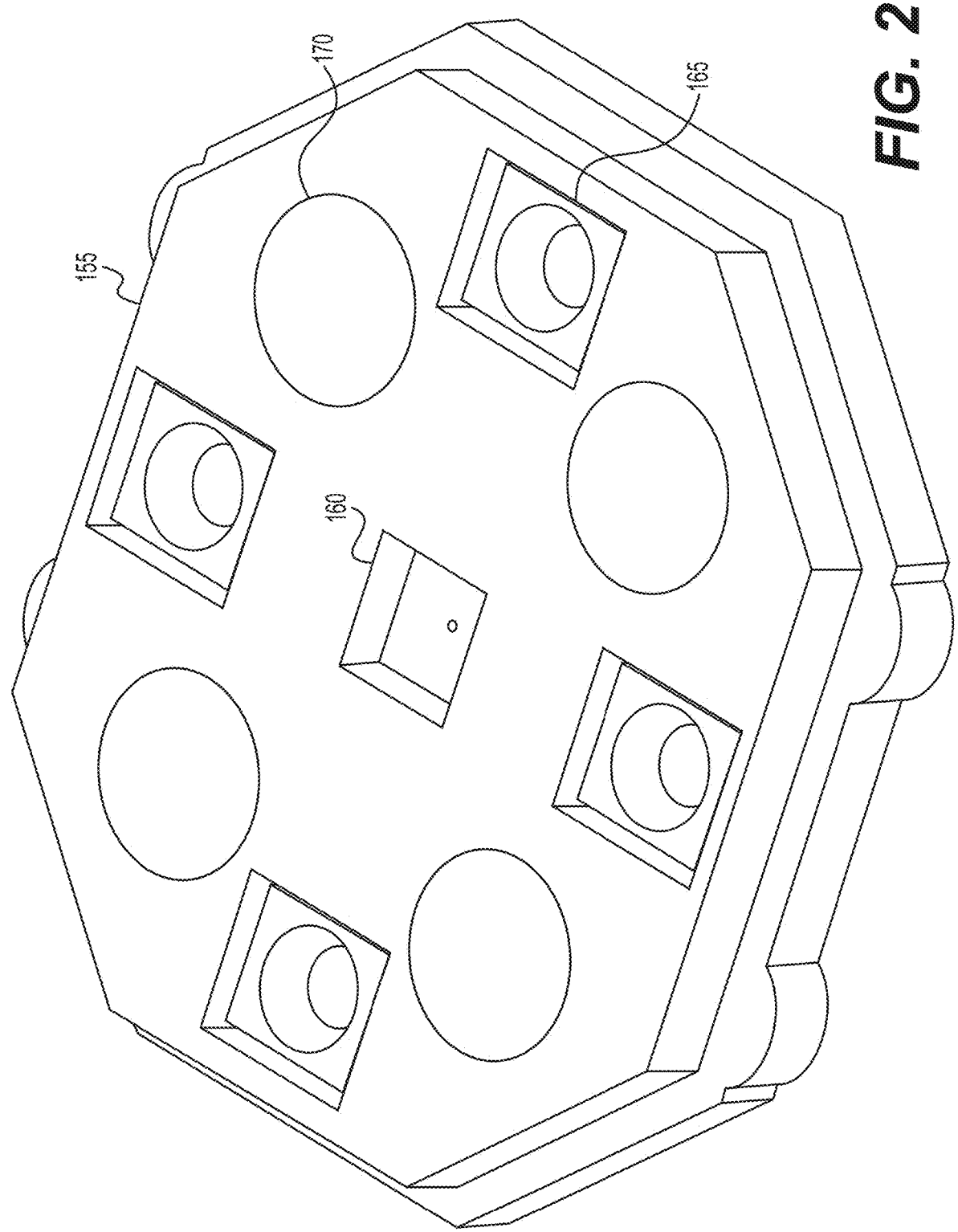
FIG. 2 depicts some aspects of an illustrative embodiment of an apparatus as described herein.

FIG. 2 depicts one embodiment of inward facing sensor array 155 of lower module 150. As shown, sensor array 155 can comprise sensors including but not limited to one or more optical detectors 160, one or more light sources 165, and one or more contact pressure/tonometry sensors 170. These sensors are only illustrative of the possibilities, however, and sensor array 155 may comprise additional or alternative sensors such as one or more acoustic sensors, electromagnetic sensors, ECG electrodes, bio impedance sensors, galvanic skin response sensors, and/or accelerometers. Upper module 110 may comprise a similar inward facing sensor array (not depicted in FIG. 1) configured to position sensors proximate or in contact with the outside portion of a user's wrist or arm. In some embodiments, sensor components of the upper and lower modules 110, 150 can be used in combination to collect and analyze physiological information. For example, and as described in more detail below, one or more light sources of lower module 150 can be used to transmit light through a targeted area of the user's tissue (e.g., a portion of the user's wrist) and the transmitted light can be detected by one or more photodetectors of an inward facing sensor array of upper module 110. In such an embodiment, opposing modules 110 and 150 can be used to detect and analyze either reflected or transmitted light.

Figure 3:
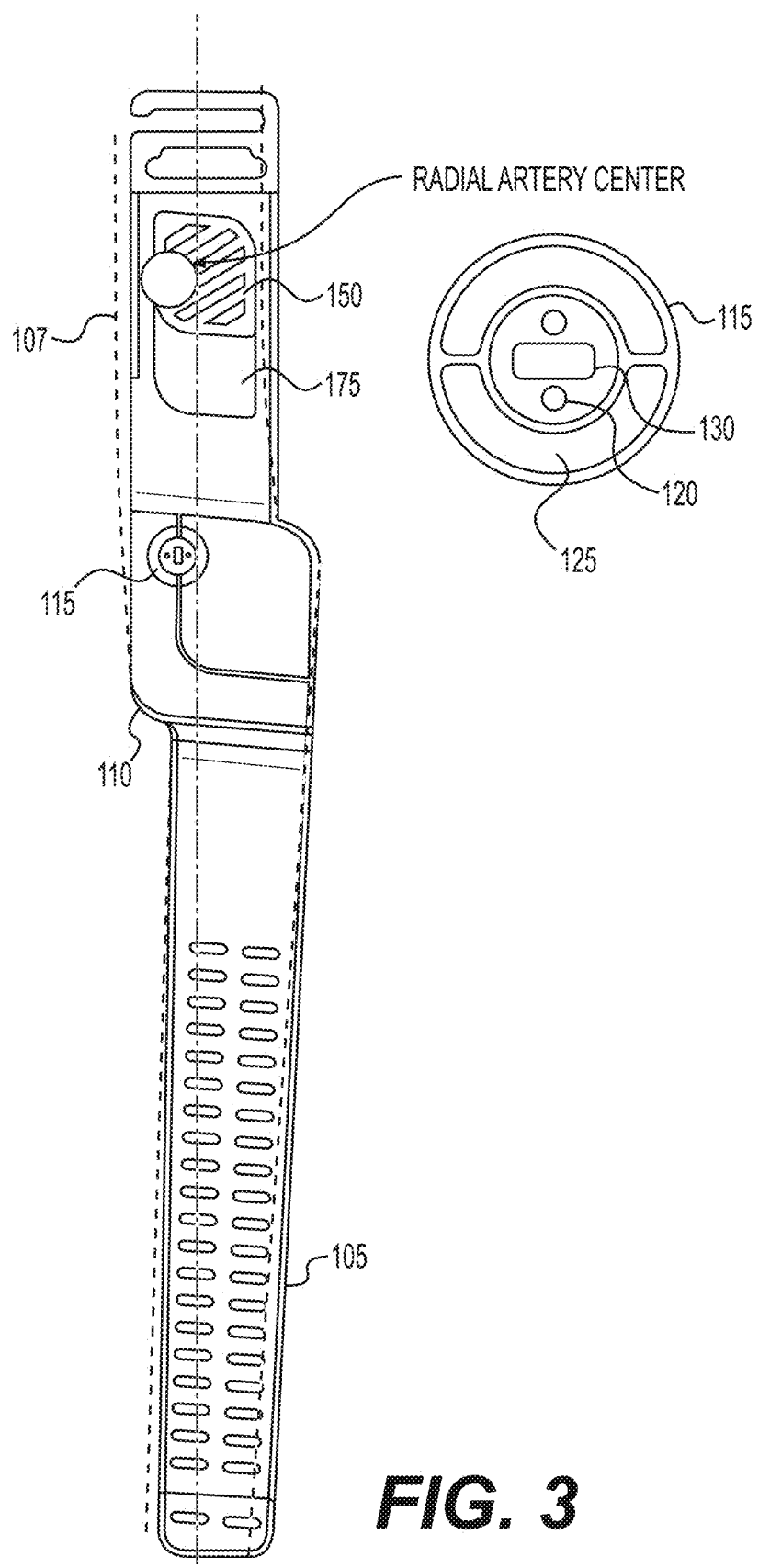
FIG. 3 depicts some aspects of an illustrative embodiment of an apparatus as described herein.

FIG. 3 depicts another view of apparatus 100 comprising band 105, upper module 110, and lower module 150. As described above, lower module 150 can be placed within channel 175 of band 105 such that lower module 150 can slide along the longitudinal axis of band 105. The movability of lower module 150 (or upper module 110 in alternative embodiments) with respect to band 105 allows a user to customize the location of the inward facing sensors of lower module 150 with respect to a targeted tissue area to ensure reliable and accurate detection of physiological parameters. For example, a user can ensure that the inward facing sensors of lower module 150 are place in a location proximate the center of the user's radial artery.

In another aspect, band 105 may not extend around the user's wrist such that it traverses a circumferential path lying in a plane perpendicular to the longitudinal axis of the user's wrist or arm. Rather, the longitudinal axis of band 105 extends at an angle such that portions of inward facing sensor arrays of upper or lower modules 110, 150 can be placed at suitable locations proximate a desired targeted area of tissue while a portion of band 105 is in contact with portions of the user's wrist or arm that the user finds comfortable (i.e., above or below the wrist joint). In some embodiments, where a circumferential path around a user's wrist resides in a plane perpendicular to the longitudinal extension of the user's arm or wrist, band 105 may be set at an angle 107 with respect to the perpendicular plane. In some embodiments, angle 107 may be between 5° and 15° with respect to the perpendicular plane. In other embodiments, angle 107 may be less than 5° or more than 15°. Of primary importance is the placement of one or more components of the sensor arrays of upper and lower modules 110, 150 proximate or in contact with a desired targeted area of tissue while allowing a portion of band 105 to be worn at a comfortable location off the user's wrist joint. Additional details regarding proper or desirable placement of one or more sensors with respect to targeted tissue areas of a user are described below with respect to other figures.

FIG. 3 also shows a closer view of outward facing sensor array 115. In the embodiment depicted, sensor array 115 may comprise one or more electrodes 120 for establishing an electrical connection with a user's fingertip and collected ECG data. Sensor array 115 may further comprise one or more contact pressure/tonometry sensors 125 for detecting the presence of the user's fingertip, which can trigger activation of electrodes 120. Sensor array 115 may also comprise additional or alternative components 130 such as one or more optical detectors, light sources, acoustic sensors, electromagnetic sensors, bio impedance sensors, galvanic skin response sensors, and/or accelerometers.

Figure 4A:
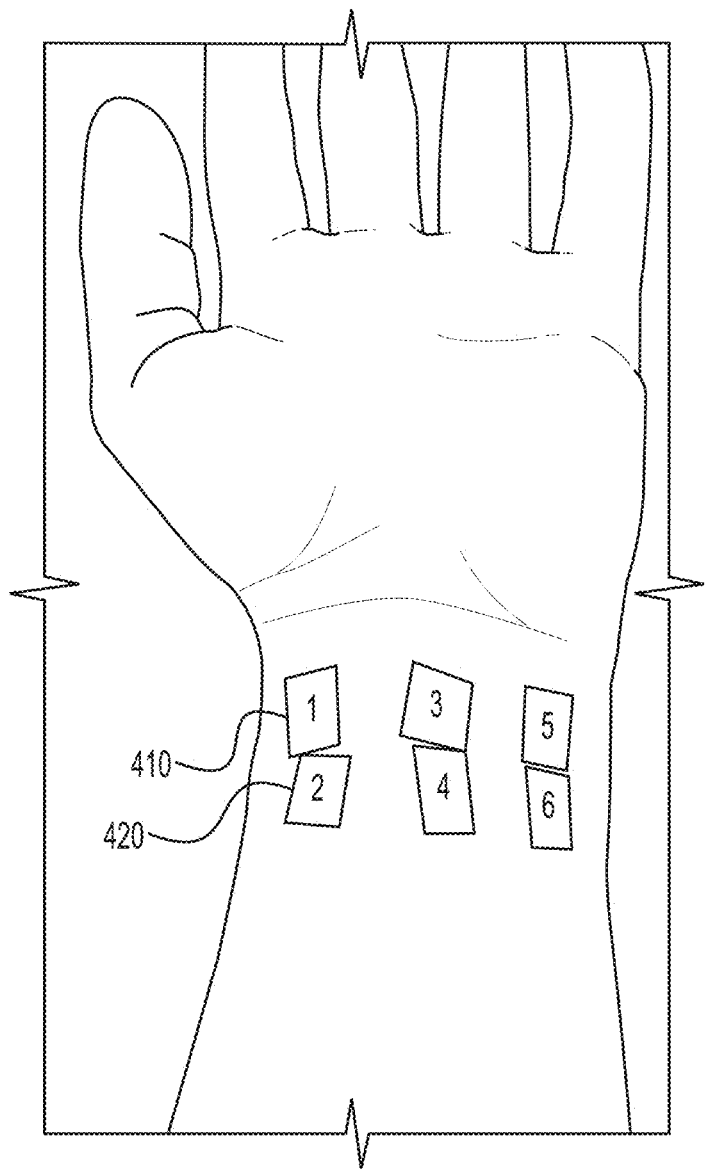
FIGS. 4A-4C depict some aspects of a user's anatomy as described herein.

FIG. 4A depicts some points of interest on a human wrist. The best point on the wrist for detecting blood flow, for example in calculating heart rate, blood pressure, respiratory rate, etc., is at a location coinciding with the wrist joint, approximately at location 1 shown as item 410. This location is proximate the radial artery and is referred to as the CUN location. Thus, the ideal location for a user to wear a wrist worn device is along the line across a line comprising locations 1-3-5. However, for comfort, most users prefer to wear straps or bands off the wrist joint, for example, across locations 2-4-6 shown as item 420. The result is that in most cases, users wear their monitors and corresponding sensors at a location on their wrist or arm that is not ideal and likely to introduce errors in the detection of physiological parameters.

The band angle 107 described with respect to FIG. 3 cures this deficiency in that it allows one or more sensor components of lower module 150 to be located above the CUN location while allowing a portion of the remaining band and/or upper module 110 to be positioned at a more comfortable location on the user's wrist or arm, such as line 2-4-6 (item 420).

Further ensuring that one or more sensors of lower module 150 can be placed at a desirable location above the CUN location, and as described in more detail above with respect to FIGS. 1 and 3, lower module 150 can slide along band 105. This allows the user to make further adjustments to the location of one or more sensors, not just along the longitudinal extension of the user's arm when apparatus 100 is in use, but also along the circumferential extension of band 105 while apparatus 100 is in use. Thus, the combination of band 105 extending around the user's wrist at an angle 107 together with the ability to slide lower module 150 along band 105, ensure the sensors of lower module 150 can be placed at an ideal location with respect to each user (even users of different body types and physical attributes) and that the physiological parameters detected and analyzed by apparatus 100 are collected as accurately as possible.

Not only is apparatus 100 configured so as to ensure proper placement of one or more sensors and comfortability of band 105, but it also may contain additional sensors, such as a pressure sensor, at locations of apparatus 100 other than upper and lower modules 110, 150. For example, apparatus 100 may comprise a pressure sensor located somewhere else along strap 105 or at a latch that secures opposing ends of band 105 around a user's wrist for detecting pressure. Such a sensor can be used to ensure that the user is wearing apparatus 100 tightly enough to ensure one more other sensors are in sufficient contact with a targeted area of the user's tissue to collect accurate physiological information. In alternative embodiments, one or more pressure sensors of the upper and/or lower modules 110, 150 can be used to make the same determination. In either case, apparatus 100 may also be configured to alert the user (for example, via display unit 112 of upper module 110) if apparatus 100 is being worn too loosely or too tightly to ensure accurate measurements.

Figure 4B:
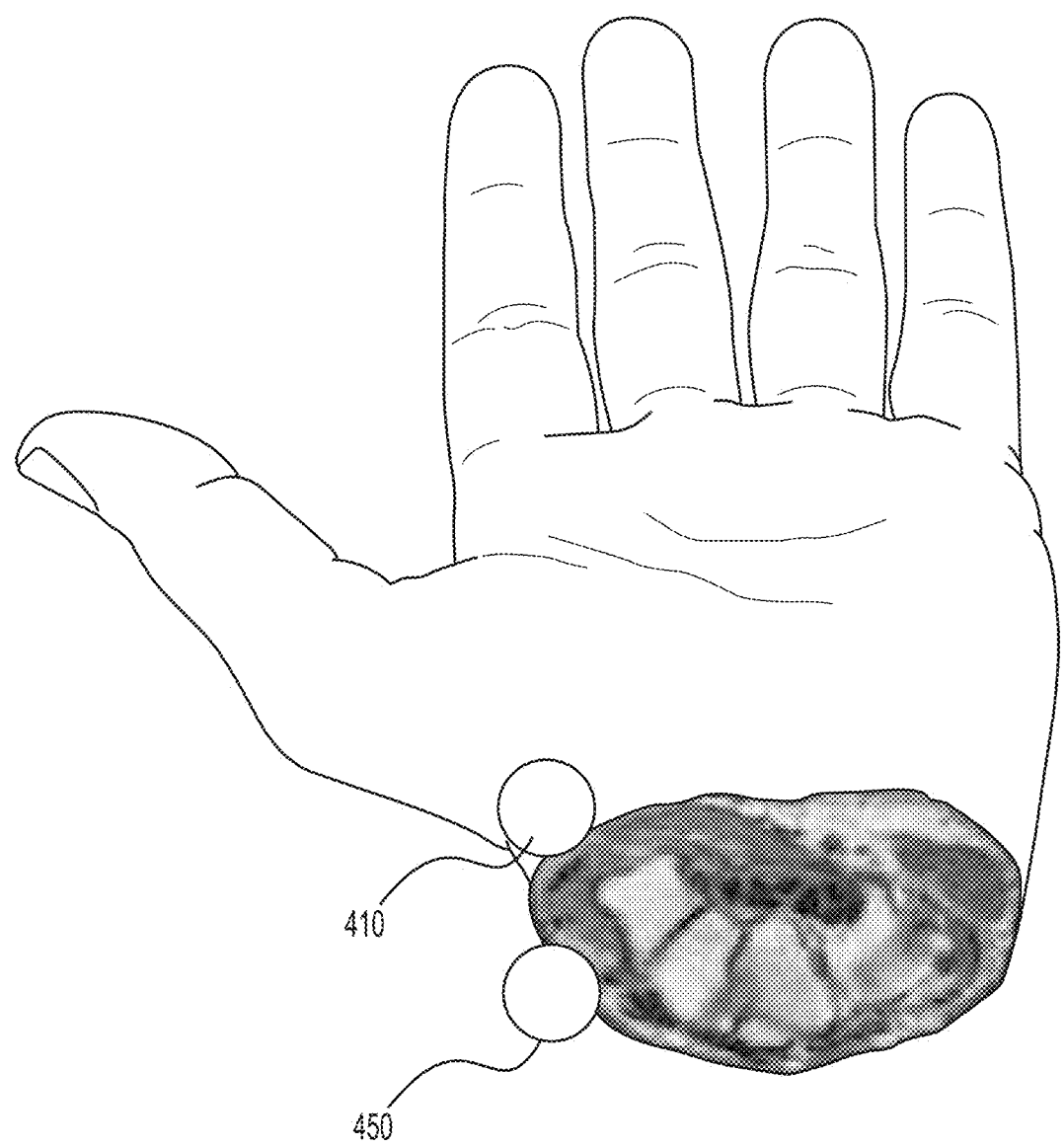

FIG. 4B depicts one example of desirable locations for one or more sensors to placed with respect to a user's wrist or other targeted area. In one embodiment, one or more sensors of lower module 150 can be placed adjacent or proximate point 410 (i.e., the CUN location) and one or more sensors of upper module 110 can be placed opposite point 410 at point 450 of the user's wrist or targeted area. Such a configuration provides the aforementioned benefits associated with proper placement of sensors over the CUN location, but also allows for apparatus 100 to detect, collect, and analyze blood flow through the radial artery using either reflective or transmissive systems.

Figure 4C:
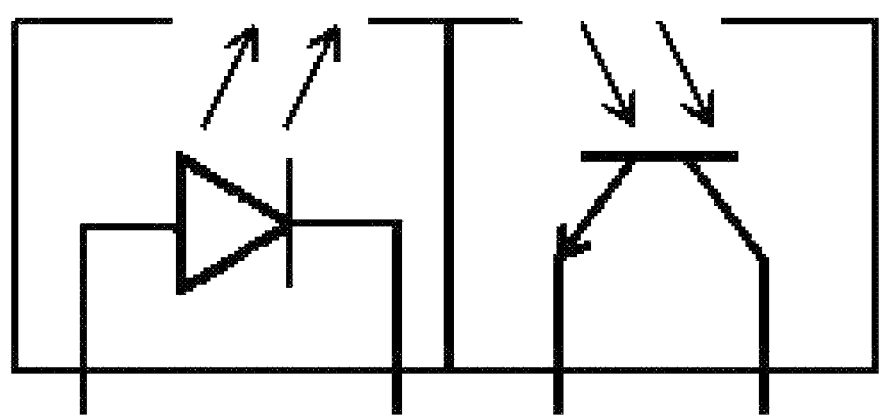

Wrist worn PPG sensors currently use a reflective system whereby a sensor array comprises one or more light sources and one or more optical detectors, located near one another and on the same side of a user's targeted area. The one or more light sources of the sensor array illuminate a portion of the user's tissue and light is reflected back to the optical detector(s) of the sensor array. The reflected light detected by the optical detector can be analyzed to estimate physiological parameters such as blood flow and pulse rate. An example schematic depicting a reflective system is shown in FIG. 4C.

However, reflective systems may not be as accurate as transmissive systems that place one or more light sources on one side of a user's body and optical detectors on an opposing side of the user's body. One example of a transmissive system are fingertip monitors used in a clinical setting. The monitors are clipped to a patient's fingertip, one side comprising a light source for illuminating the top or bottom of the patient's fingertip, the other side comprising an optical detector for detecting the light transmitted through the fingertip.

It has been thought that transmissive systems are not practical for wrist worn health monitors (or monitors worn at other locations on a user's arm or body) because the wrist is too thick for light that enters one side of a targeted area to be transmitted all the way through to the other side. However, apparatus 100 solves this problem by taking advantage of the natural location of the CUN location (the location of the radial artery at the wrist) at the inside of the wrist just under the thumb. As shown in FIGS. 5A, 5B, and 5C, apparatus 100 can be configured to place lower module 150 comprising a light source (and/or optical detector) at the location of the CUN artery on the underside of the wrist and place the upper module 110 comprising an opposing optical detector (or light source) at a location opposite the sensors of the lower module at the periphery of the outside of the wrist just below the thumb. In this manner, the path of light transmitted through the wrist between the sensors of the lower and upper modules travels a shorter distance (shown in FIG. 4B) than if the sensors were located closer to the center of the inside and outside of a user's wrist. As a result, light illuminated from either the upper or lower module can be detected at the opposing module in a manner previously only available in clinical settings and limited to locations on the body such as the fingertip.

As described above, apparatus 100 may comprise a number of components and sensors for detecting physiological information and extracting data from it, such as blood flow, heart rate, respiratory rate, blood pressure, steps, calorie expenditure, and sleep.

ECG electrodes/sensors, bio impedance sensors, galvanic skin response sensors, tonometry/contact sensors, accelerometers, pressure sensors, acoustic sensors, and electromagnetic sensors One method for determining the heart rate, respiratory rate, blood pressure, oxygen levels, and other parameters of a user involves collecting a signal indicative of blood flow pulses from a targeted area of the user's tissue. As described above, this information can be collected using, for example, a light source and a photo detector. Some embodiments may use multiple light sources and they may be of varying colors. For example, one light source may be an IR light source and another might be an LED light (such as a red LED). Using both an IR light source and a colored LED light (such as red) can improve accuracy as red light is visible and most effective for use on the surface of the skin while IR light is invisible yet effective for penetration into the skin. Such embodiments may comprise multiple photo detectors, one or more configured to detect colored LED light (such as red) and one or more configured to detect IR light. These photo detectors (for detecting light of different wavelengths) can be combined into a single photodiode or maintained separate from one another. Further, the one or more light sources and one or more photodetectors could reside in the same module (upper or lower) in the case of a reflective system or the light source(s) could reside in one module while the optical detector(s) reside in the other in the case of a transmissive system.

Upon collection of a blood flow pulse signal, a number of parameters can be extracted from both single pulses and a waveform comprising multiple pulses. FIG. 6A depicts a single pulse from which a number of features or parameters can be extracted. Features or parameters extracted from a single pulse can include, but are not limited to, shape of the pulse, a maximum amplitude, a minimum amplitude, a maximum derivative, a time difference between main and secondary peaks, and integral through the entire extraction time (i.e., the area under the pulse). FIGS. 6B and 6C illustrate that even portions of a single pulse can be analyzed for feature extraction. Extracting features at this level of detail has a number of advantages, including the ability to capture a great number of pulse features and store each of those features digitally without having to retain the analog waveform. The result is a savings in storage requirements and ease of data transmission.

Figure 7:
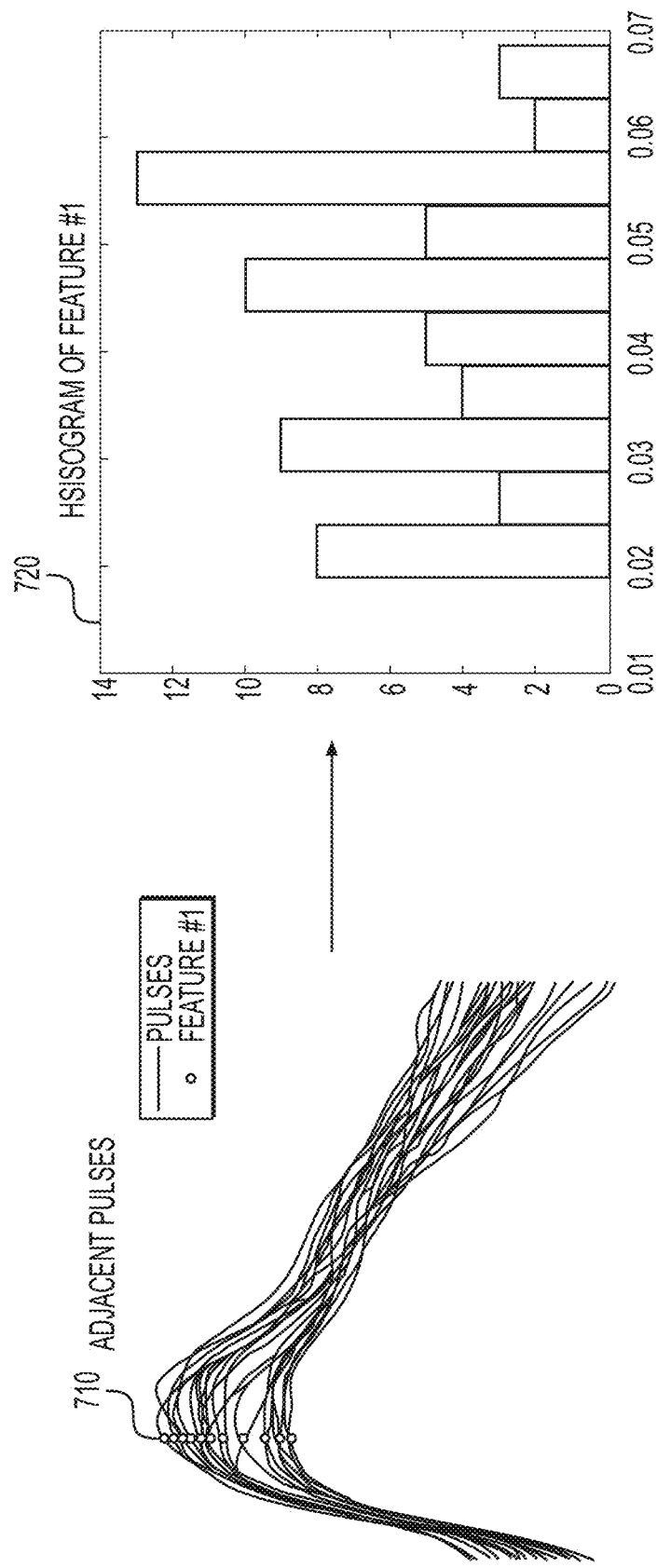
FIG. 7 depicts some aspects of an illustrative embodiment of an apparatus as described herein.

Feature extraction can also be performed on a number of pulses or a "pulse train." FIG. 7 depicts a series of pulses overlaid with one another to show the variation among the group with respect to an identified feature. In this manner, the total variation among a series of pulses with respect to a single feature can be determined. The average of a group of pulses with respect to a single feature and the standard deviation of the group with respect to the feature can also be determined. Of course, these are just examples of the types of information that can be collected from a comparison of a single feature over a group of pulses. Moreover, while FIG. 7 depicts the extraction of a single feature from the group of pulses, it should be appreciated that any number of features can be extracted from the group in a manner similar to that described above with respect to a single pulse. FIG. 7 further depicts how information collected about a single feature over a group of pulses can be digitized or presented in a histogram 720.

All of the features or parameters described above, collected using a PPG system comprising one or more light sources and/or one or more optical detectors, can be supplemented with additional sensors such as ECG electrodes/sensors, bio impedance sensors, galvanic skin response sensors, tonometry/contact sensors, accelerometers, pressure sensors, acoustic sensors, and electromagnetic sensors. For example, one or more tonometry/contact sensors can be used to extract tonometry information by measuring the contact vessel pressure. In another example, one or more acoustic sensors comprising a speaker-microphone combination (such as a micro-electro-mechanical system ("MEMS") acoustic sensor) can be used to extract reflected sound pulses from moving vessel walls. Similarly, one or more electromagnetic sensor MEMS can be used to extract voltage induced by coils or magnet pieces pressed to moving vessel walls. In a further embodiment, as described above, external or outward facing sensors can be configured to activate when touched by the off-hand (i.e., the hand on which apparatus 100 is not being worn) to collect additional information to help supplement or calibrate the information collected by the inward facing sensors of the upper or lower modules. For example, where internal facing PPG components (i.e., one or more light sources and one or more photo detectors) are used to detect reflected or transmitted light representative of blood flow pulses and some extrapolation of the data is made to determine, for example, heart rate, the user can place a fingertip of his or her off-hand on an outward facing ECG electrode (such as that shown in FIG. 1) to collect a more precise heart rate measurement. The more precise, though of more finite duration, heart rate measurement can be used to aid in the interpretation of the continuous heart rate measurements collected by the inward facing PPG sensors. The outward facing sensor can also comprise other sensors previously described herein, such as one or more contact/tonometry sensors, one or more bio impedance sensors, and one or more galvanic skin response sensors for analyzing electric pulse response. All of the information collected by an outward facing sensor from, for example, the fingertip of the user's off-hand, can be used to refine the analysis of the continuous measurements taken by any one or more of the inward facing sensors.

In addition to the inward and outward facing sensors, apparatus 100 may further comprise additional internal components such as one or more accelerometers and/or gyroscopic components for determining whether and to what extent the user is in motion (i.e., whether the user is walking, jogging, running, swimming, sitting, or sleeping). Information collected by the accelerometer(s) and/or gyroscopic components can also be used to calculate the number of steps a user has taken over a period of time. This activity information can also be used in conjunction with physiological information collected by other sensors (such as heart rate, respiration rate, blood pressure, etc.) to determine a user's caloric expenditure and other relevant information.

To determine a user's blood pressure, the PPG information described above may be combined with other sensors and techniques described herein. In one embodiment, determining a user's blood pressure can comprise collecting a heart rate signal using a PPG system (i.e., one or more light sources and photo detectors) and performing feature extraction (described above) on single pulses and a series of pulses. The features extracted from single pulses and series of pulses can include statistical averages of various features across a series, information regarding the morphological shape of each pulse, the average and standard deviation of morphology of a series of pulses, temporal features such as the timing of various features within single pulses, the duration of a single pulse, as well as the average and standard deviation of the timing of a feature or duration of pulses within a series of pulses, and the timing of morphological features across a series of pulses (i.e., the frequency with which a particular pulse shape occurs in a series).

As described above, this feature extraction can not only be performed on a series of pulses and single pulses, but also on portions of a single pulse. In this manner, information pertaining to both systolic and diastolic blood pressure can be ascertained as one or more portions of an individual pulse correspond to the heart's diastole (relaxation) phase and one or more other portions of an individual pulse correspond to the heart's systole (contraction) phase. In some embodiments, up to 60 features can be extracted from a partial pulse, a single pulse, and/or a series of pulses. In alternative embodiments, fewer or more features may be extracted.

In addition to features extracted from PPG or ECG information, information and features can also be collected by contract/tonometry sensors, pressure sensors, bio impedance sensors galvanic skin response sensors, accelerometers, acoustic sensors, and electromagnetic sensors. For example, pressure sensors or bio impedance sensors can be used to identify blood flow pulses of user and, similar to PPG or ECG data, features can be extracted from the collected data.

The extracted features can then be cross-referenced or compared to entries in a library containing data corresponding to a population of subjects. For each subject, the library may contain information associated with each extracted feature. The library can also contain a direct measured or verified blood pressure for each subject. In further embodiments, the library may contain more than one directly measured or verified blood pressure measurement for each subject, each corresponding to a subject in a different condition, such as one corresponding to the subject at rest, one corresponding to the subject engaged in light activity, and one corresponding to the subject engaged in strenuous activity. Thus, the extracted features of the user, as well as activity information pertaining to the user, can be compared to entries in the library to find one or more subjects with which the user's extracted features most closely compare and the user's blood pressure can then be estimated based on the verified blood pressure of those subjects.

As one example, when features are extracted from a series of pulses, a standard deviation or range of variation across the series can be ascertained. Generally speaking, a large variation across a series of pulses can be associated with flexible, healthy veins. As a result, individuals exhibiting large pulse-to-pulse variations across a series of pulses typically have relatively low blood pressure. Conversely, little to no variation in features across a series of pulses is typically associated with relatively high blood pressure.

The library described above can be generated by extracting the same features from partial pulses, individual pulses, and series of pulses across hundreds or thousands of subjects. The subjects' verified blood pressure can also be measured such that it can be associated with each feature extracted from the subject's pulse information. The subject entries in the library can also be sorted based on information helpful for estimating blood pressure. For example, subjects in the library can be identified as male or female, belonging to a particular age group, or associated with one or more past health conditions. Individual subjects can be associated with information indicative of the subject's sex, age, weight, race, and any other medically meaningful distinction. Moreover, entries can be associated with information collected by other sensors at the time the verified blood pressure measurement was taken, including information collected by contract/tonometry sensors, pressure sensors, bio impedance sensors galvanic skin response sensors, accelerometers, acoustic sensors, and electromagnetic sensors. As just one example, if a user is determined to be engaged in physical activity (through a combination of accelerometer and heart rate data, as an example), his or her extracted features may only be compared to data in the library corresponding to subjects engaged in similar physical activity. Information pertaining to subjects contained in the library may also be correlated to each subject's resting heart rate, BMI, or some other medically significant indicia. For example, if a user is a young female with a low resting heart rate who is currently engaged in moderate activity, her extracted features should be compared to subjects in the library identified as young females with low resting heart rate whose blood pressure was verified during moderate activity rather than comparing the user's extracted features to an elderly male subject with a relatively high resting heart rate and whose blood pressure was verified during strenuous activity.

When the user's extracted features are compared to features recorded in the library, apparatus 100 can also weigh the entries of subjects most closely corresponding to the user more heavily than entries of subjects associated with indicia different from that of the user. For example, if the user is a male, features extracted from male subjects may be weighed more heavily than female subjects because a particular pulse variation in men of a particular age may correspond to relatively high blood pressure whereas the same pulse variation in women of that particular age may correspond to lower blood pressure.

According to the techniques described herein, accurate blood pressure estimates for a user can made without requiring direct blood pressure measurement of the user. However, in some embodiments, the user's blood pressure estimates can be further calibrated by direct measurement of the user's blood pressure by another device and that verified blood pressure can be input into apparatus 100 to aid in future estimations of the user's blood pressure.

Calibration can also be accomplished with an outward facing ECG sensor. While an inward facing PPG sensor can continuously or periodically collect heart rate data of a user, occasionally the user may be prompted to place a fingertip of his or her off-hand on an outward facing ECG sensor (e.g., electrodes). The inward facing sensor arrays of apparatus 100 may contain additional electrodes thereby completing an electrical circuit through the user's body and allowing a more precise pulse waveform to be collected. Feature extraction can be performed on these pulses, series of pulses, and partial pulses in the same manner as described above with respect to PPG information and used to cross-reference the library.

In still a further embodiment, where apparatus 100 determines, based on its continuous or periodic monitoring of the user's blood pressure using PPG or pressure sensors, that a user's blood pressure is unusually or dangerously high or low, apparatus 100 may prompt the user to place a fingertip of his or her off-hand on an outward facing ECG electrode in order to verify the unusual or unsafe condition. If necessary, apparatus 100 can then alert the user to call for help or seek medical assistance.

As described above, the upper and/or lower modules 110, 150 can be configured to continuously collect data from a user using its inward facing sensor arrays. However, certain techniques can be employed to reduce power consumption and conserve battery life of apparatus 100. For instance, in some embodiments, only one of the upper or lower modules 110, 150 may continuously collect information. In alternative embodiments, neither module may be continuously active, but may wait to collect information when conditions are such that accurate readings are most likely. For example, when one or more accelerometers or gyroscopic components of apparatus 100 indicate that a user is still, at rest, or sleeping, one or more sensors of upper and/or lower module 110, 150 may collect information from the user while artifacts resulting from physical movement are absent.

While techniques for estimating a user's blood pressure using pulse signal, pressure, impedance, and other collected and input information has been described above, it should be appreciated that similar techniques can be employed to estimate a user's oxygen levels ($SvO_2$), hydration, respiration rate, and heart rate variability. For example, PPG, ECG, bio impedance, and acoustic measurements taken from the user can be cross-referenced with the aforementioned library and compared to subjects most closely matching the user (e.g., sex, age, height, weight, race, resting heart rate, BMI, current activity level, and any other medically meaningful distinction. Measured or verified hydration levels of one or more subjects can then be used to estimate the hydration level of the user. A similar process can be employed to estimate the user's oxygen levels ($SvO_2$), respiration rate, and heart rate variability.

FIG. 8 depicts an illustrative processor-based computing system 800 representative of the type of computing system that may be present in or used in conjunction with any aspect of apparatus 100 comprising electronic circuitry. Each of upper or lower modules 110, 150 may comprise any one or more components of system 800. In some embodiments, one module may contain one of the components of system 800 and the other module, rather than comprising a similar component, may be in wired or wireless communication with the component residing in the other first module. Alternatively, each module may comprise a similar component as compared to the other module such that it is not necessary to communication with the first module to enjoy the functionality of the component. For example, upper module 110 may comprise storage, a power source, and/or a charging port, while lower module 150 may have access to the upper module's storage and/or draw power from the power source of the upper module through a wired or wireless connection. Alternatively, each module may have its own storage and/or power source. For the sake of simplicity, computing system 800 will be described herein as if it encompasses the components of upper and lower modules 110, 150 collectively, while the reader appreciates that one or more components described herein may reside only in one module or may be found in both modules.

Processor-based computing system 800 may be used in conjunction with any one or more of transmitting signals to and from the one or more accelerometers, sensing or detecting signals received by one or more sensors of apparatus 100, processing received signals from one or more components or sensors of apparatus 100 or a secondary device, and storing, transmitting, or displaying information. Computing system 800 is illustrative only and does not exclude the possibility of another processor- or controller-based system being used in or with any of the aforementioned aspects of apparatus 100.

In one aspect, system 800 may include one or more hardware and/or software components configured to execute software programs, such as software for storing, processing, and analyzing data. For example, system 800 may include one or more hardware components such as, for example, processor 805, a random access memory (RAM) module 810, a read-only memory (ROM) module 820, a storage system 830, a database 840, one or more input/output (I/O) modules 850, an interface module 860, and one or more sensor modules 870. Alternatively and/or additionally, system 800 may include one or more software components such as, for example, a computer-readable medium including computer-executable instructions for performing methods consistent with certain disclosed embodiments. It is contemplated that one or more of the hardware components listed above may be implemented using software. For example, storage 830 may include a software partition associated with one or more other hardware components of system 800. System 800 may include additional, fewer, and/or different components than those listed above. It is understood that the components listed above are illustrative only and not intended to be limiting or exclude suitable alternatives or additional components.

Processor 805 may include one or more processors, each configured to execute instructions and process data to perform one or more functions associated with system 800. The term "processor," as generally used herein, refers to any logic processing unit, such as one or more central processing units (CPUs), digital signal processors (DSPs), application specific integrated circuits (ASICs), field programmable gate arrays (FPGAs), and similar devices. As illustrated in FIG. 8, processor 805 may be communicatively coupled to RANI 810, ROM 820, storage 830, database 840, I/O module 850, interface module 860, and one more sensor modules 870. Processor 805 may be configured to execute sequences of computer program instructions to perform various processes, which will be described in detail below. The computer program instructions may be loaded into RAM for execution by processor 805.

RAM 810 and ROM 820 may each include one or more devices for storing information associated with an operation of system 800 and/or processor 805. For example, ROM 820 may include a memory device configured to access and store information associated with system 800, including information for identifying, initializing, and monitoring the operation of one or more components and subsystems of system 800. RAM 810 may include a memory device for storing data associated with one or more operations of processor 805. For example, ROM 820 may load instructions into RAM 810 for execution by processor 805.

Storage 830 may include any type of storage device configured to store information that processor 805 may need to perform processes consistent with the disclosed embodiments.

Database 840 may include one or more software and/or hardware components that cooperate to store, organize, sort, filter, and/or arrange data used by system 800 and/or processor 805. For example, database 840 may include user profile information, historical activity and user-specific information, physiological parameter information, predetermined menu/display options, and other user preferences. Alternatively, database 840 may store additional and/or different information.

I/O module 850 may include one or more components configured to communicate information with a user associated with system 800. For example, I/O module 850 may comprise one or more buttons, switches, or touchscreens to allow a user to input parameters associated with system 800. I/O module 850 may also include a display including a graphical user interface (GUI) and/or one or more light sources for outputting information to the user. I/O module 850 may also include one or more communication channels for connecting system 800 to one or more secondary or peripheral devices such as, for example, a desktop computer, a laptop, a tablet, a smart phone, a flash drive, or a printer, to allow a user to input data to or output data from system 800.

Interface 860 may include one or more components configured to transmit and receive data via a communication network, such as the Internet, a local area network, a workstation peer-to-peer network, a direct link network, a wireless network, or any other suitable communication channel. For example, interface 860 may include one or more modulators, demodulators, multiplexers, demultiplexers, network communication devices, wireless devices, antennas, modems, and any other type of device configured to enable data communication via a communication network.

System 800 may further comprise one or more sensor modules 870. In one embodiment, sensor modules 870 may comprise one or more of an accelerometer module, an optical sensor module, and/or an ambient light sensor module. Of course, these sensors are only illustrative of a few possibilities and sensor modules 870 may comprise alternative or additional sensor modules suitable for use in apparatus 100. It should be noted that although one or more sensor modules are described collectively as sensor modules 870, any one or more sensors or sensor modules within apparatus 100 may operate independently of any one or more other sensors or sensor modules. Moreover, in addition to collecting, transmitting, and receiving signals or information to and from sensor modules 870 at processor 805, any one or more sensors of sensor module 870 may be configured to collect, transmit, or receive signals or information to and from other components or modules of system 800, including but not limited to database 840, I/O module 850, or interface 860.

While embodiments have been illustrated and described, it will be appreciated that various changes can be made therein without departing from the spirit and scope of the disclosure. Moreover, the various features of the embodiments described herein are not mutually exclusive. Rather any feature of any embodiment described herein may be incorporated into any other suitable embodiment.

Additional features may also be incorporated into the described systems and methods to improve their functionality. For example, those skilled in the art will recognize that the disclosure can be practiced with a variety of physiological monitoring devices, including but not limited to heart rate and blood pressure monitors, and that various sensor components may be employed. The devices may or may not comprise one or more features to ensure they are water resistant or waterproof. Some embodiments of the devices may hermetically sealed.

Other embodiments of the aforementioned systems and methods will be apparent to those skilled in the art from consideration of the specification and practice of this disclosure. It is intended that the specification and the aforementioned examples and embodiments be considered as illustrative only, with the true scope and spirit of the disclosure being indicated by the following claims.

What is claimed is:

1. A wearable device for collecting a pulse signal of a user comprising:
   at least one module comprising:
      at least one light source;
      an inward facing sensor array; and
      an outward facing sensor array, wherein each of the inward facing sensor array and the outward facing sensor array comprise at least one electrocardiogram (ECG) electrode; and
   a strap extending from the at least one module at an angle so that when the strap is used to secure the at least one module to a portion of a user's wrist, the at least one light source can be positioned above a radial artery at the user's wrist while at least a portion of the strap is positioned away from the user's wrist, wherein the strap extends from the upper module at an angle of between 5 degrees and 15 degrees so that when the strap is secured to the user a circumferential extension of a band lies in a plane that is not perpendicular to a line corresponding to a longitudinal extension of the arm of the user.

2. The device of claim 1, wherein the at least one module comprises a first module comprising the at least one light source and a second module comprising at least one photo detector.

3. The device of claim 2, wherein the pulse signal is determined based on light transmitted through a portion of the user's wrist.

4. The device of claim 3, wherein the portion of the user's wrist is an edge of the user's wrist offset from a longitudinal extension of an arm of the user.

5. The device of claim 1, wherein the at least one module further comprises one or more of an ECG electrode, a bio impedance sensor, a galvanic skin response sensor, a contact sensor, an accelerometer, a pressure sensor, an acoustic sensor, and an electromagnetic sensor.

6. The device of claim 1, wherein the ECG electrode of the inward facing sensor array is configured for contact with a portion of the user's wrist and the ECG electrode of the outward facing sensor is configured for contact with a portion of a fingertip of the user.

7. The wearable device of claim 1, wherein the strap comprises an aperture within which the lower module can slide relative to a longitudinal extension of the strap.

8. An apparatus for determining a physiological parameter of a user comprising:
   an upper module;
   a lower module; and
   a strap configured to secure the upper and lower module to a user's wrist,
   wherein the upper module comprises a first sensor array on an inward facing surface of the module configured for contact with a first targeted area of the user and a second sensor array on an outward facing surface of the module;
   wherein the lower module comprises a third sensor array on an inward facing surface of the module configured for contact with a second targeted area of the user,
   wherein the strap extends from the upper module at an angle of between 5 degrees and 15 degrees so that when the strap is secured to the user a circumferential extension of a band lies in a plane that is not perpendicular to a line corresponding to a longitudinal extension of the arm of the user.

9. The apparatus of claim 8, wherein the first targeted area of the user is located on an outside of an arm of the user proximate to the user's wrist.

10. The apparatus of claim 8, wherein the second targeted area of the user is located on the inside of an arm of the user proximate the user's wrist.

11. The apparatus of claim 8, wherein the lower module is located on the strap so that the third sensor array is configured for contact with a radial artery of a wrist of the user.

12. The apparatus of claim 11, wherein the strap comprises an aperture within which the lower module can slide relative to a longitudinal extension of the strap.

13. The apparatus of claim 8, wherein the third sensor array comprises at least one light source for illuminating a targeted area of tissue of the user and the first sensor array comprises a photo detector for detecting light transmitted through a portion of the user's tissue.

14. The apparatus of claim 8, wherein the first and second sensor arrays each comprise one or more electrodes, the one or more electrodes of the first sensor array configured for contact at the user's arm to which the apparatus is secured and the one or more electrodes of the second sensor array configured for contact with a fingertip of the user on an opposing arm.

* * * * *